United States Patent [19]

Kremer et al.

[11] Patent Number: 5,649,935
[45] Date of Patent: Jul. 22, 1997

[54] ULTRASONIC PERCUSSION DEVICE

[75] Inventors: Daniel Kremer, Combes la Ville; Gérard Drobinski, Fontenay aux Roses, both of France

[73] Assignee: Aerospatiale Societe Nationale Industrielle, Paris, France

[21] Appl. No.: 377,856

[22] Filed: Jan. 25, 1995

[30] Foreign Application Priority Data

Feb. 3, 1994 [FR] France ................... 94 01201

[51] Int. Cl.$^6$ ................... A61B 17/22
[52] U.S. Cl. ................... 606/128; 606/169; 604/22
[58] Field of Search ................... 606/128, 169; 604/22; 279/43.3, 46.3; 24/135 N, 135 R, 136 B; 439/268

[56] References Cited

U.S. PATENT DOCUMENTS

| 1,905,452 | 8/1933 | Eaton | 439/269 |
|---|---|---|---|
| 4,854,325 | 8/1989 | Stevens | 606/128 |
| 5,156,143 | 10/1992 | Bocquet et al. | 606/128 |
| 5,243,997 | 9/1993 | Uflacker et al. | 128/772 |

FOREIGN PATENT DOCUMENTS 0 424 231  4/1991  European Pat. Off. .

Primary Examiner—Robert A. Hafer
Assistant Examiner—Benjamin K. Koo
Attorney, Agent, or Firm—Marshall, O'Toole, Gerstein, Murray & Borun

[57] ABSTRACT

The invention relates to an ultrasonic percussion device, of the type including:

- an ultrasonic wave generator, terminated by an unit (6) transmitting the vibration generated;
- a wire (8), the near end of which is carried by said unit and the far end of which is set into percussive movement; and
- linking means (7) for immobilizing the near end of said wire in said generator unit.

According to the invention, said unit (6) is produced from an elastically deformable material and said linking means (7) are formed on said unit in such a way as to form an integral part of the latter, said linking means being capable of occupying a spontaneously close-together position, for which the near end (8A) of said wire (8) is clamped by said unit, and a position deliberately spaced apart by actuation means (14) for which the near end (8A) of said wire can be freed from said unit or engaged in said unit.

12 Claims, 2 Drawing Sheets

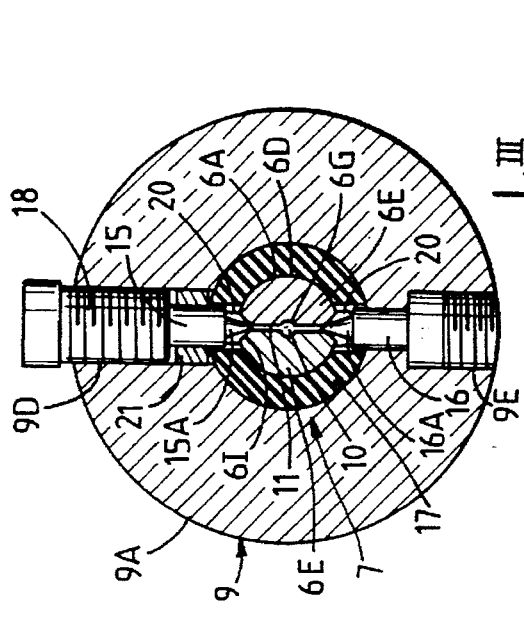
FIG.1
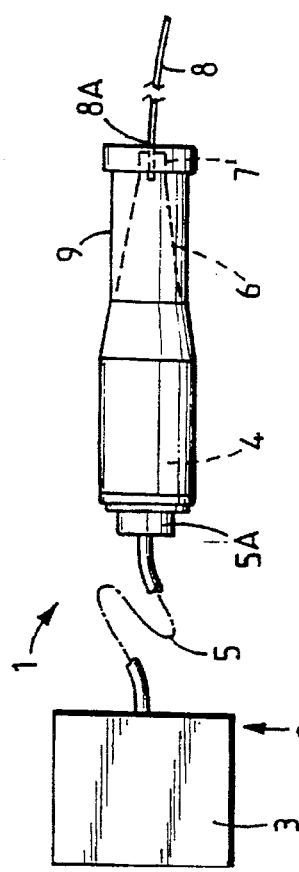
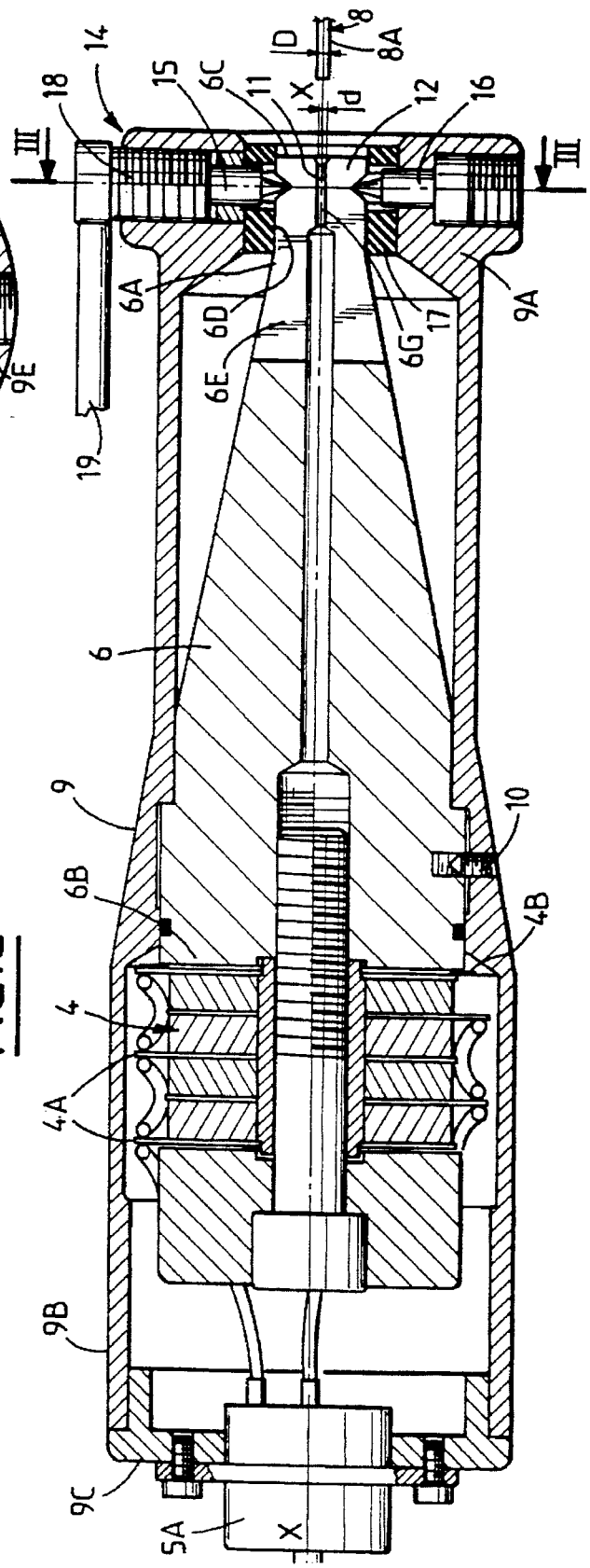
FIG.3
FIG.2

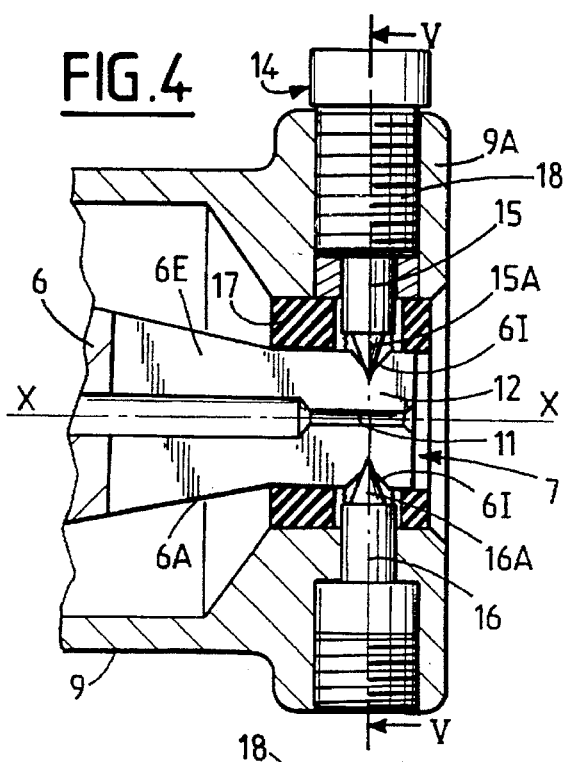
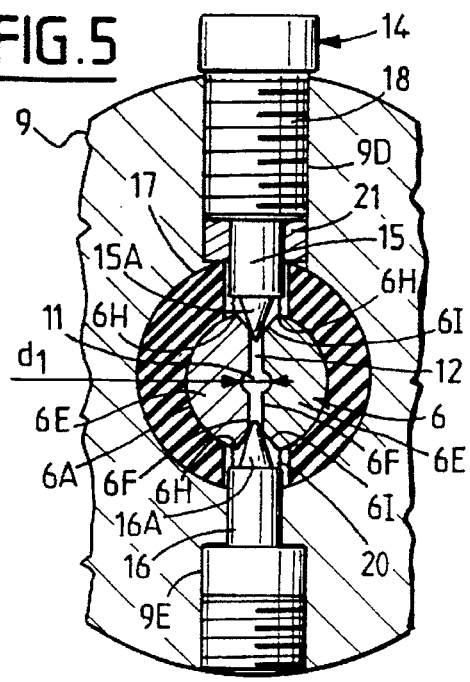
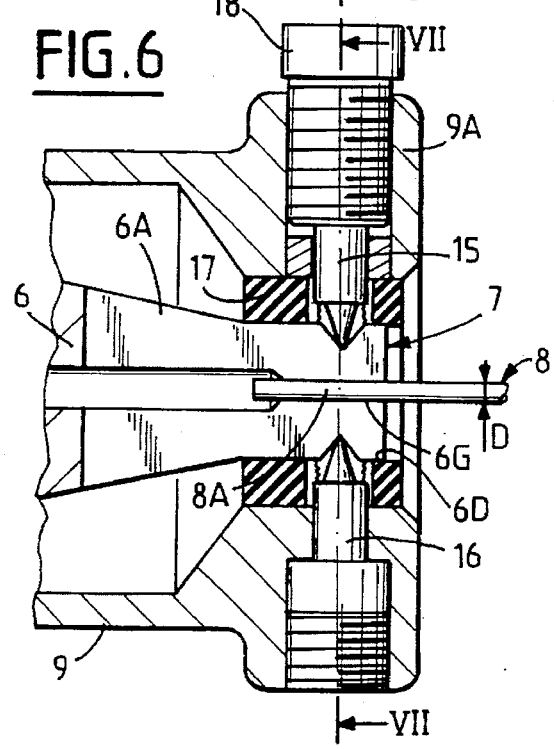
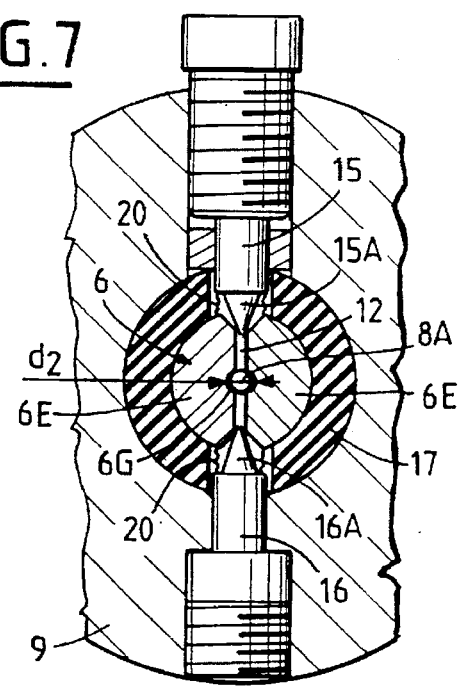
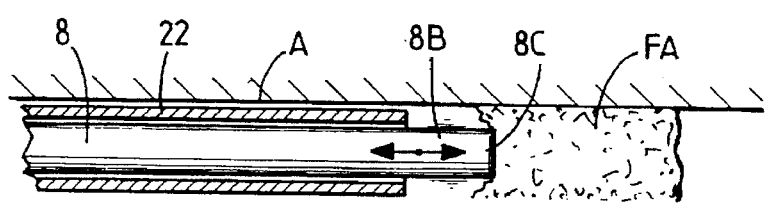

ULTRASONIC PERCUSSION DEVICE

BACKGROUND OF THE INVENTION

The present invention relates to an ultrasonic percussion device intended more particularly, although not exclusively, for medical applications relating to treatment of body canals or morphological ducts, such as, for example, the destruction of atheromas inside arteries. Obviously, it goes without saying that the percussion device could be used for other applications, particularly industrial applications such as machining, polishing, unblocking of pipes, etc., without departing from the scope of the invention.

It is known that, for destroying atheromas, one of the techniques available to the practitioner consists in using ultrasonic percussion devices which generally comprise:

an ultrasonic wave generator, terminated by an unit transmitting the vibration generated;

a wire, the near end of which is carried by said unit and the far end of which is set into percussive movement; and linking means for immobilizing the near end of said wire in said generator unit.

Thus, by means of the generator, the vibration generated is transmitted to the wire which is inserted by the practitioner into the body canal to be treated, and the far end of which cyclically pounds the atheroma to be destroyed.

As the preamble to the French patent 2 653 040 stresses, the major drawback of these devices relates to their linking means which do not provide maximum transmission of the vibration to the wire, by reason of its millimetric diameter and of the functional play which results therefrom. Thus, the invention described in the patent consists in remedying that by proposing linking means which comprise:

a sleeve which is radially deformable in an elastic way, accommodating the near end of said wire and provided with a conical flared part;

a bore provided in said transmission unit and into which said sleeve is inserted, the conical part of said sleeve coming into contact with a complementary conical wall formed in said bore; and a clamping element interacting by screwing with said unit and acting against said sleeve, so that, when the screw is tightened, the conical part of said sleeve is pressed against the conical wall of said bore causing, by radial deformation of said sleeve, clamping of the near end of said wire, until said clamping element comes into contact with a stop provided on said unit.

Although percussion devices equipped with these linking means give effective results as far as the treatment proper is concerned, that is to say to destruction of atheromas, it nevertheless proves to be awkward to use them as far as manipulation of them is concerned. In fact, on the one hand, it is necessary to screw the clamping element (a nut) tightly onto the said unit by means of attached keys, which is not appreciated by the practitioners. Moreover, jamming arises between the sleeve and the near end of the wire, which sometimes prevents them being manually dismantled, mainly because of surface defects and of the inevitable matting of the latter.

SUMMARY OF THE INVENTION

The object of the present invention is to remedy these drawbacks, and it relates to an ultrasonic percussion device, the linking means of which make it possible to keep the wire on said unit without having recourse to significant clamping, nor to attached tools, and while ensuring maximum transmission of said vibrations.

To this end, the ultrasonic percussion device, of the previously described type, is noteworthy, according to the invention, in that said unit is produced from an elastically deformable material and in that said linking means are formed on said unit in such a way as to form an integral part of the latter, said linking means being capable of occupying a spontaneously close-together position, for which the near end of said wire is clamped by said unit, and a position deliberately spaced apart by actuation means, for which the near end of said wire can be free from said unit or engaged into said unit.

Thus, by virtue of its design in an elastically deformable material, said unit terminating the ultrasonic wave generator can be used directly as linking means, which makes it possible particularly to dispense with the usual pieces which constitute them (clamping element and sleeve previously used) in order to fix the wire to the device, and with the drawbacks which they engender as reviewed above.

For preference, said linking means form part of the free end of said unit, opposite its other end linked to said generator, and they are, for example, defined by a passage, formed in said free end of said unit from its transverse face, and able to accommodate the near end of said wire, and by at least one longitudinal slot formed at the end of said free end, from its outer lateral surface up to said passage, in order to shape it into an elastically deformable slotted end. Thus, the slot contributes to making the free end of said unit elastically deformable, which constitutes gripping jaws for clamping the near end of the wire, with a constant force, by the internal lateral surface delimiting the passage.

In order to do that, said passage initially exhibits a diameter less than the diameter of said wire, in such a way that, when said actuation means are operated, said linking means with slotted end occupy the deliberately spaced-apart position in order to allow said wire to be inserted into said passage then exhibiting a diameter greater than that of said wire, and, when said actuation means are released, said linking means occupy the spontaneously close-together position, in order to allow clamping of the near end of the wire by pinching.

More particularly, said unit exhibits an axisymmetric cylindrical shape, and said passage is situated axially in said unit, from the transverse face of its free end, while said longitudinal slot opens out in line with said passage. For preference, said longitudinal slot traverses the free end of said unit from end to end, passing through said passage, so as to separate it into two identical parts. Obviously, it would be equally possible to form two diametral longitudinal slots, perpendicular to each other, or more, in order to separate the free end into four identical parts, or even three radial longitudinal slots, regularly spaced by 120° with respect to one another, in order to separate the free end into three identical parts.

According to another characteristic of the invention, the device moreover comprises a hollow body surrounding said unit and advantageously bearing said actuation means at one of its ends vertically in line with said linking means. This body moreover allows the practitioner to manipulate the device.

For example, said actuation means can comprise at least one movable spacing piece which is lodged in a hole provided radially in the corresponding end of said hollow body, and which faces said slot, said piece being capable of penetrating into said slot in order to space apart the lateral faces which delimit it and to enlarge said passage, when it is actuated.

For preference, when said longitudinal slot diametrally traverses the free end of said unit from end to end, said actuation means comprise, facing respectively opposed lateral edges delimiting said slot, a movable spacing piece and a fixed spacing piece, said pieces being lodged respectively in opposed radial holes provided in the corresponding end of said hollow body. The two pieces could also be movable.

Advantageously, between the free end of said unit and the corresponding end of said body, a damping sleeve is provided, made of elastomer or the like, traversed by the spacing piece or pieces. In that way, vibration of the assembly is avoided, the body being isolated from the unit. In particular, said spacing piece is radially movable toward the slot by a pressure screw which is lodged in said body in order to act on said piece, and which can be operated by a handle or the like external to said body.

Thus, the actuation of the linking means is easily performed by the practitioner who can act on the handle of the spacing means while holding the body of the percussion device, without having to resort to attached tools.

Moreover, said spacing piece or pieces are terminated by conical points capable of engaging in substantially complementary imprints formed in the lateral edges delimiting said slot. The spacing-apart of said parts of the free slotted end is thus facilitated. Also, around said spacing piece or pieces, o-rings or the like are arranged between the pieces and the outer lateral surface of said free end of said unit. These o-rings play the role of return spring for said pieces after they have been actuated, avoiding contact by the conical points with the unit in the course of the operation of the latter.

The figures of the attached drawing will give a good understanding of how the invention can be produced. In these figures, identical references designate similar elements.

BRIEF DESCRIPTION OF THE DRAWINGS

FIG. 1 diagrammatically represents an ultrasonic percussion device in accordance with the invention.

FIG. 2 shows, in axial section, an embodiment example of the unit of said generator before the mounting of the wire.

FIG. 3 is a view in section along the line III—III of FIG. 2.

FIG. 4 shows, in enlarged partial axial section, the linking means of said unit, in spaced-apart position, for mounting of said wire.

FIG. 5 is a view in section along the line V—V of FIG. 4.

FIG. 6 shows, in enlarged partial axial section, the linking means of said unit, in spontaneously close-together position, for clamping of said wire.

FIG. 7 is a view in section along the line VII—VII of FIG. 6.

FIG. 8 diagrammatically illustrates the action of the far end of said wire on the atheroma to be destroyed.

DETAILED DESCRIPTION OF A PREFERRED EMBODIMENT

The ultrasonic percussion device 1, represented in FIG. 1, comprises an ultrasonic wave generator 2 of a type which is known in itself, including an electrical high-frequency generator 3 and a piezoelectric converter 4 linked together by an electrical link 5. A unit 6 for transmitting the vibration produced is associated with the converter 4 and, by way of linking means 7, it carries the near end 8A of a wire 8, the far end 8B of which is capable of being inserted, in this preferential application, of a body canal to be treated, in order to come into contact with a deposit to be destroyed, such as an atheromatous formation for example. The destruction of the latter is achieved by the generator 2 which converts the electrical energy produced into mechanical energy, by said converter, which is transmitted by said unit 6 along said wire 8 in the form of mechanical vibrations, the far end 8B of which encyclically pounds the atheromatous formation.

In order to transmit this vibratory mechanical energy intact to the wire, the transmission unit 6 is produced from an elastically deformable material and the linking means 7 are advantageously incorporated in the unit 6. As FIG. 2 shows, the unit 6 has an axisymmetric cylindrical shape, with longitudinal axis X-X and its free or downstream end 6A then defines the means of linking of the near end 8A of the wire. At the opposite, upstream end 6B of the unit the piezoelectric converter 4 is attached which particularly includes supply washers 4A and at least one insulant 4B. The assembly consisting of the unit 6 and of the converter 4 is accommodated in a hollow cylindrical body 9, secured to the unit by screws 10 and allowing the practitioner to manipulate the device 1.

More particularly, the unit 6 exhibits a somewhat conical shape towards its free end 6A, in which are formed a passage 11, from its transverse face 6C, and a longitudinal slot 12 which, in this embodiment example, traverses the free end 6A from end to end, passing through the middle via the passage 11. As can be seen in FIGS. 2 and 3, this longitudinal slot 12 diametrally opens out of the outer lateral surface 6D of the free end 6A, and separates the latter into two identical parts 6E, the cross-section of which is semicircular. The longitudinal slot 12 has a spacing, lying between the parallel opposed faces 6F of the identical parts 6E, less than the diameter d of the passage 11, the inner lateral surface 6G of Which, delimited by the two parts 6E, is intended to hold the near end 8A of the wire by pinching, as will be seen later. This diameter d is initially less than the diameter D of the wire which, according to the types of canals and of ducts to be treated, may have a value lying between 0.2 mm and 0.5 mm. In these figures, the dimensions of the passage and of the wire have been exaggerated for reasons of clarity in the figures.

It will thus be understood that the axial passage 11, the longitudinal slot 12 and the parts 6E of the free end 6A of said unit which result therefrom form the integrated linking means 7 for allowing clamping by pinching, at a constant force, of the near end 8A of the wire, by elastic deformation of said slotted free end of said unit. In particular, the parts 6E of the linking means 7 may occupy a spontaneously close-together position, for which the near end of the wire is clamped by the unit 6 (FIGS. 6 and 7) and a position deliberately spaced apart, a way of actuation means 14, for which the near end of the wire can be freed from the unit or engaged in the latter (FIGS. 4 and 5).

Moreover, the hollow cylindrical body 9, surrounding the transmission unit 6 and the piezoelectric converter 4 carries the actuation means 14 at its end 9A situated around the free end 6A of said unit, and, at its other end 9B, a cover 9C in which is connected the plug 5A of the electrical link 5 linking the generator 3 to the converter 4.

Structurally, the actuation means 14 are defined, in this embodiment, by two cylindrical spacing pieces 15 and 16 which are lodged respectively in radial diametrally opposed holes 9D and 9E, provided in the end 9A of the body 9, and which are situated opposite the longitudinal slot 12, respectively on either side of the latter. More particularly, between the end 9A of the body and the free end 6A of the unit a damping sleeve 17 is arranged, produced from elastomer and of then annular section. This sleeve 17 is traversed radially by the spacing pieces, the flexible link thus created between the two ends of the unit and of the body avoids the assembly vibrating. The piece 15 is, for example, radially movable in the direction of the slot 12, while the piece 16 can be mounted fixed into the hole 9E. In order to facilitate engaging the spacing pieces in the slot, between the lateral edges 6H which delimit it laterally, conical points 15A and 16A respectively terminate the pieces 15 and 16 so as to be in proximity with conical imprints 6I which are formed in the lateral edges 6H of the end 6A and in which the said conical points are arranged. The spacing piece 15 is made movable by virtue of a pressure screw 18 which is lodged in the hole 9D then tapped at this location in order to act on the piece 15. This screw 18 can be controlled by a handle 19, to which it is linked and which is advantageously accessible externally to said body 9. This embodiment of the actuation means 14 is particularly advantageous since the practitioner, carrying the body 9, can easily carry out the fitting and/or the removal of the near end of a wire by directly maneuvring the handle 19. As for the other spacing piece 16, it is screwed directly into the tapped hole 9E so as to be immobilized there, in such a way that its conical point 16A is set in proximity to the conical imprint 6I.

Moreover, o-rings 20 or the like are provided around the conical points 15A and 16A of the spacing pieces, between the outer lateral surface 6D of the free end 6A of said unit and the spacing pieces 15 and 16. The movable spacing piece 15 is, moreover, lodged in the hole 9D of the body by means of a guide ring 21.

Putting the near end 8A of a wire 8 in place within the transmission unit 6 of the device 1 progresses in the following way. First of all, the linking means 7, situated at the free end 6A of the transmission unit 6, occupy the initial position illustrated in FIGS. 2 and 3, for which the diameter d of the passage is a minimum, less than the diameter D of the wire.

In order to carry out insertion of the near end of the wire, the practitioner acts on the handle 19 of the actuation means 14 which, by means of the screw 18, move the spacing piece 15, radially with respect to the axis X-X, the conical point 15A of the spacing piece being applied on the corresponding conical imprint 6I so as to open the slot 12, by spacing apart the identical parts 6E of the slotted end 6A. The radial action of the spacing piece 15, by means of the elastic sleeve 17, produces a slight displacement of the end 6A in the same direction, which has the effect of engaging the opposite conical imprint 6I in the conical point 16A of the fixed piece 16 and, thus, of participating in the spacing of the parts 6E of the unit. As FIGS. 4 and 5 show, the linking means 7 then occupy a position deliberately spaced apart under the action of the means 14, for which the passage has a diameter d1 greater than the diameter D of the wire via the elastic deformation of the parts 6E of the free end of said unit, the conical points spacing apart the opposed faces 6F of said slot.

At this moment, the near end 8A of the wire is inserted into the passage 11 thus spaced apart, up to the desired site, then the actuation means 14 are released, which has the effect of radially distancing the spacing pieces 15 and 16 from the lateral edges 6H of the slot 12. Simultaneously, the parts 6E of the transmission unit, that is to say the linking means 7, come closer together so as to occupy the spontaneously close-together position, in such a way that the inner surface 6G of the passage 11 plays the role of gripping jaws, clamping the near end 8A of the wire by pinching with a constant force, as FIGS. 6 and 7 show. In this position, the diameter d2 of the passage is equal to the diameter D of the wire and it is close to the initial diameter d.

The advantages procured by the embodiment of the linking means incorporated in the elastically deformable free end of said unit relate to the constancy of the clamping force since it is independent of the practitioner, the easier manipulation by the actuation means, the absence of locking of the wire in the unit and the simpler design of said linking means.

In FIG. 8 a part of an artery A blocked, for example, by an atheromatous formation FA has been represented.

In order to eliminate this formation, the practitioner firstly inserts a sheath 22 into the artery A up to the vicinity of the atheromatous formation FA. This sheath 22 provides guidance for the wire 8 in the artery, protecting its inner wall from the rubbing by the wire, which could cause heating and harmful burning of the artery.

When the transverse face 8C of the far end 8B of the wire is substantially in contact with the atheromatous formation FA, the ultrasonic device 1 according to the invention is set into action, the vibration generated being transmitted optimally to the wire 8 by virtue of the linking means 7 previously described and incorporated into the transmission unit 6.

The vibration of the wire transmitted longitudinally acts against the atheromatous formation with an alternating movement (double arrow). During the forward movement of the wire, the face 8C of the far end 8B strikes the formation FA in order progressively to cause crumbling and fragmentation of the latter. In contrast, during the backward movement of the wire, the particles of the atheromatous formation are progressively removed from the atheroma by underpressure or cavitation effects.

By way of example, the unit 6 can be produced from an appropriate elastically deformable steel, while the body 9 is produced from a material which is preferably electrically insulating, such as polyvinyl chloride.

We claim:

1. An ultrasonic percussion device, comprising:
   an ultrasonic wave generator;
   a unit coupled to said ultrasonic wave generator for generating ultrasonic vibrations;
   a wire having a near end, a far end, and a diameter; and
   linking means, coupled to said unit, for immobilizing said near end of said wire and allowing said far end of said wire to vibrate due to said ultrasonic vibrations generated by said unit, said linking means comprising a pair of gripping members composed of a single, unitary piece of an elastically deformable material for gripping said wire, said gripping members occupying an unstressed position in which said gripping members are spaced apart by a distance less than said diameter of said wire and a stressed position in which said gripping members are spaced apart by a distance greater than said diameter of said wire.

2. The device as claimed in claim 1, additionally comprising actuation means having a first position in which said gripping members are maintained in said stressed position to allow said wire to be inserted into said passage and a second position in which said gripping members grip said wire.

3. The device as claimed in claim 2, wherein said linking means has a passage of variable diameter formed therein, a first end coupled to said unit, and a second end having a slot formed therein, wherein said slot separates said gripping members, and wherein said diameter of said passage is relatively large when said gripping members are in said stressed position and wherein said passage is relatively small when said gripping members are in said unstressed position.

4. The device as claimed in claim 3, wherein said unit is axisymmetric, wherein said passage is situated along a longitudinal axis of said unit, and wherein said passage intersects said slot.

5. The device as claimed in claim 3, wherein said slot separates said second end of said linking means into two identical parts.

6. The device as claimed in claim 3, additionally comprising a body disposed around said unit, said actuation means being disposed at an end of said body adjacent said second end of said linking means.

7. The device as claimed in claim 6, wherein said actuation means comprises at least one movable actuator which is disposed in a hole in said body, said movable actuator having an actuating position in which said movable actuator penetrates said slot in order to space apart said gripping members.

8. The device as claimed in claim 7, wherein said movable actuator is radially movable toward said slot by a pressure screw which is threadably disposed in said body.

9. The device as claimed in claim 7, wherein said slot has a conical indentation and wherein said movable actuator has a conical end portion which abuts said conical indentation.

10. The device as claimed in claim 6, wherein said actuation means comprises a movable actuator which is disposed in a first hole in said body and a fixed actuator disposed in a second hole in said body, said second hole being aligned with said first hole, said movable actuator having an actuating position in which said movable actuator penetrates said slot in order to space apart said gripping members.

11. The device as claimed in claim 3, additionally comprising a damping sleeve disposed around said gripping members.

12. The device as claimed in claim 6, additionally comprising an O-ring disposed around said movable actuator.

* * * * *